United States Patent [19]

McCarty

[11] 4,153,636
[45] May 8, 1979

[54] DEUTERATED ANALOGUES OF METHOXYFLURANE USEFUL AS AN ANESTHETIC

[75] Inventor: Leslie P. McCarty, Midland, Mich.

[73] Assignee: The Dow Chemical Company, Midland, Mich.

[21] Appl. No.: 759,943

[22] Filed: Jan. 17, 1977

[51] Int. Cl.$^2$ ............ C07C 43/00; C07C 43/12; A61K 31/08
[52] U.S. Cl. ............................ 568/684; 424/342
[58] Field of Search ........................... 260/614 F

[56] References Cited

U.S. PATENT DOCUMENTS 3,104,202  9/1963  Larsen .................. 260/614 F X
3,216,897  11/1965  Krantz .................. 260/614 F X Primary Examiner—Howard T. Mars
Attorney, Agent, or Firm—James W. Ambrosius

OTHER PUBLICATIONS

Hitt et al., Isotopic Probe of the Mechanism of Methoxyflurane Defluorination, 2 pages.

[57] ABSTRACT

Deuterated analogues of methoxyflurane and a method of their use as an anesthetic.

2 Claims, No Drawings

DEUTERATED ANALOGUES OF METHOXYFLURANE USEFUL AS AN ANESTHETIC

BACKGROUND OF THE INVENTION

Methoxyflurane, 2,2-dichloro-1,1-difluoro-1-methoxy-ethane, is a commonly used general inhalation anesthetic. U.S Pat. No. 3,104,202. A major drawback of this compound is the renal dysfunction which may result from its use. *J. Am. Med. Assn.* 216, 278–288 (1971). Studies have shown a dose related nephrotoxicity in rats anesthetized with methoxyflurane. *Anesthesiology* 36, 571–587 (1972). Such toxicity is related to the presence of inorganic fluoride released into the blood serum by the metabolic degradation of the methoxyflurane. *Anesthesiology* 35, 286–292 (1971) and *Anesthesiology* 33, 579–593 (1970).

It is known that the replacement of hydrogen by deuterium in some antimicrobial compounds will result in a marked decrease in enzymatic defluorination. See 15th Interscience Conf. of Antimicrobials, Agents and Chemotherap., September 24–26, 1975, Abstract Nos. 100, 101, and 102.

SUMMARY OF THE INVENTION

It has been discovered that certain deuterated analogues of methoxyflurane decrease the metabolism of the compound to inorganic fluorides when the deuterated analogue is inhaled by an animal, especially a mammal. The placement of the deuterium atoms in the molecule was found to be critical and apparently unexpectedly is species specific, since one deuterated methoxyflurane analogue was found upon inhalation by an animal to actually undergo an increase in enzymatic defluorination thereof raising the concentration of inorganic fluorides in the serum of the animal.

Two deuterated analogues were found to decrease the amount of metabolized inorganic fluoride from that realized only from methoxyflurane in the serum as measured by total fluoride present in the urine following anesthesia. The structures of these compounds are as follows:

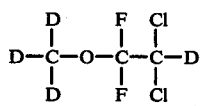

hereafter MF-$D_4$ or 2,2-dichloro-1,1-difluoro-1-methoxy-$d_3$-ethane-d, and

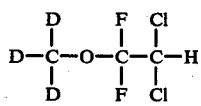

hereafter MF-$D_3$ or 2,2-dichloro-1,1-difluoro-1-methoxy-$d_3$-ethane.

A third analogue having the structure

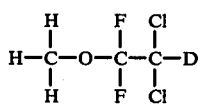

hereafter MF-D or 2,2-dichloro-1,1-difluoro-1-methoxy-ethane-d was found to increase total inorganic fluoride output in the urine.

The compound 2,2-dichloro-1,1-difluoro-1-methoxy-$d_3$-ethane, i.e., MF-$D_3$, is particularly preferred, and when inhaled by an animal showed the lowest concentration of inorganic fluoride in the urine.

As used herein, the term "animal" refers to an inhalation anesthetic susceptible animal.

In anesthetizing an animal using the compounds and method of the present invention, the compound is usually administered by vaporizing the compound in the presence of an innocuous gas vaporization medium such as, for example, helium, nitrogen, oxygen or various mixtures thereof. The compound may also be in combination with other anesthetics such as nitrous oxide; for example.

From the foregoing discussion, it is seen that the deuterated analogues of methoxyflurane, MF-$D_4$ and MF-$D_3$, have substantially the same desirable anesthetic effects as methoxyflurane, but are not as readily metabolized to inorganic fluorides by an animal which has inhaled them. Accordingly, it would be expected that the possiblity of renal dysfunction resulting from the presence of inorganic fluorides in the serum and urine would be significantly reduced by using MF-$D_4$ or MF-$D_3$ as an anesthetic.

DETAILED DESCRIPTION OF THE INVENTION

The following examples will serve to further clarify the present invention but are not to be construed as a limitation thereon.

EXAMPLE 1

Preparation of 2,2-dichloro-1,1-difluoro-1-methoxy-$d_3$-ethane-d (MF-$D_4$)

Dowex-21K ® (Dow) resin in the Cl form was converted to the OH— form by washing the beads with 10% hydrated potassium hydroxide. The beads were washed with methanol and dried on a rotary-vacuum stripper.

The dried resin (10 grams) was charged along with 20 grams (0.56 mole) of fully deuterated methanol ($CD_3OD$) into a 250 ml round bottom flask equipped with a magnetic stirrer and cooled in an ice bath. Approximately 80 grams (0.6 mole) of 1,1-difluoro-2,2-dichloroethylene was slowly bubbled into the flask over a period of about three hours. After this time, the ice bath was removed and the flask sealed and allowed to warm to room temperature overnight.

The resin was filtered away from the solution, and bromine was added dropwise to destroy any excess olefin. The solution was washed with water and distilled through a vigreux column. A center cut boiling at 50°–51° C./110 mm Hg was confirmed as containing about 95% 2,2-dichloro-1,1-difluoro-1-methoxy-$d_3$-ethane-d using NMR data as compared to an external standard.

EXAMPLE 2

Preparation of 1,1-difluoro-2,2-dichloro-1-methoxy-$d_3$-ethane (MF-$D_3$)

Dowex-21K ® (Dow) resin prepared in the manner of Example 1 above was charged into a 3-necked 250 ml round bottom flask fitted with a large efficient condenser, thermometer, addition tube, and magnetic stirrer. Deuterated methanol ($CD_3OD$) (30 ml, 0.67 mole)

was added to the flask and cooled in an ice bath. To this mixture, 110.0 grams (0.827 mole) of 1,1-difluoro-2,2-dichloroethylene (about a 20% excess) was added. The reaction vessel was capped, allowed to warm slowly to room temperature, and maintained at about 22° C. for 18 hours.

The reaction mixture was separated from the resin beads by vacuum distillation at 10 mm Hg. The liquid obtained was mixed with 50 ml of 10% potassium hydroxide and refluxed for 0.5 hours and then separated by fractional distillation at atmospheric pressure. A proton NMR spectrum of a sample of collected material indicated the proton on the $O-CF_2CCl_2D$ group had been exchanged by hydrogen to about 80%. The 1,1-difluoro-2,2-dichloro-1-methoxy-$d_3$-ethane was brominated to a yellow color (about 3 drops of $Br_2$) and distilled under reduced pressure. The boiling point of the product was found to be 50° C. at 100 mm Hg.

EXAMPLE 3

Metabolism studies for inorganic fluoride following use of methoxyflurane deuterated analogues described hereinbefore were carried out as follows. Methoxyflurane, as a control, and MF-$D_3$, MF-$D_4$ and MF-D deuterated analogues thereof were vaporized by metering the liquid compounds at a controlled rate into a temperature regulated vaporization flask held at 150° C. The vapor was swept into the air inlet of a 30 liter glass exposure chamber at a rate of 6 liters/minute. The concentration of the anesthetic in the exposure chamber was monitored by gas-liquid chromatography using direct gas sampling loops.

Groups of 6 male Fischer 344 rats (6 months of age, 200–300 grams) were exposed to room air and 0.5% volume/$_{volume}$ of methoxyflurane and each of the three deuterated analogues described above for a period of 2 hours. After the exposure, room air was passed through the chamber for 30 minutes before the animals were removed. All animals were maintained in individual metabolism cages for 48 hours after exposure. Urine was collected during each of two 24 hour intervals after exposure. Urinary volume for each animal was recorded and the urine samples were assayed for inorganic fluoride using an Orion fluoride electrode.

A comparison of the amount of total inorganic fluoride in the urine of the test animals receiving the deuterated compounds as compared to controls receiving methoxyflurane is shown in Table I below.

TABLE I

| Compound | % Change in Fluoride* |
|---|---|
| MF-D | +43% |
| MF-$D_3$ | −34% |
| MF-$D_4$ | −29% |

*as compared to control animals treated with methoxyflurane.

The data indicate, on the basis of residual inorganic fluoride in the urine following anesthesia that the compound 2,2-dichloro-1,1-difluoro-1-methoxy-$d_3$-ethane (MF-$D_3$) is the anesthetic of choice with the compound 2,2-dichloro-1,1-difluoro-1-methoxy-$d_3$-ethane-d (MF-$D_4$) also showing a desirable significant reduction in the amount of inorganic fluoride in the urine.

In this study, no difference in the anesthetic properties of methoxyflurane and its deuterated analogues was noted.

It is understood that various modifications may be made in the exact mode of carrying out the present invention without departing from the spirit and scope thereof. While the foregoing description has been directed to rats, it will be realized by one skilled in the art that the compounds 2,2-dichloro-1,1-difluoro-1-methoxy-$d_3$-ethane and 2,2-dichloro-1,1-difluoro-1-methoxy-$d_3$-ethane-d may be used with equal facility on other inhalation anesthetic susceptible animals.

As noted above, the methoxyflurane analogues MF-$D_4$ and MF-$D_3$ are not as readily metabolized to inorganic fluoride as measured in the urine of a mammal which has inhaled the compounds when compared to mammals which have inhaled methoxyflurane or the analogue MF-D. While the inventor does not wish to limit his invention to any particular mechanism, the following proposed model is given to clarify the invention in light of the present art. This scheme is not to be taken as a limitation on the scope of the present invention.

Two major metabolites, methoxydifluoroacetic acid and dichloroacetic acid, have been found to result from the enzymatic degradation of methoxyflurane. On the basis of this knowledge, the metabolic degradation of methoxyflurane could have two major pathways leading to the elimination of the above metabolites. The proposed scheme is as follows:

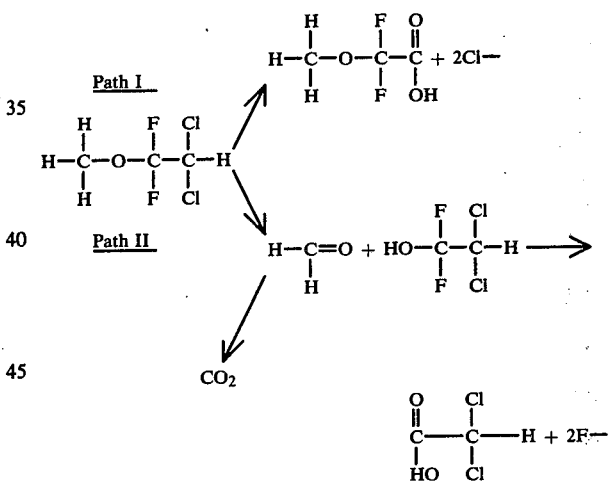

Assuming the proposed scheme is correct, then anesthesia with MF-D would decrease metabolism along Path I and force metabolism along Path II which would result in higher inorganic fluoride in the serum. This is what has been observed. Anesthesia using the fully deuterated MF-$D_4$ or the analogue MF-$D_3$ would either decrease the metabolism of the compounds generally so that the compound is eliminated unchanged or alternatively increase the metabolism along Path I leading to less toxic metabolites and lower levels of inorganic fluoride.

I claim:
1. The compound 2,2-dichloro-1,1-difluoro-1-methoxy-$d_3$-ethane-d.
2. The compound 2,2-dichloro-1,1-difluoro-1-methoxy-$d_3$-ethane.

* * * * *